(12) United States Patent
Katayama

(10) Patent No.: US 7,035,377 B2
(45) Date of Patent: Apr. 25, 2006

(54) X-RAY GENERATOR AND ADJUSTING METHOD OF THE SAME

(75) Inventor: Chuji Katayama, Yokohama (JP)

(73) Assignee: Bruker AXS K.K., Tsukuba (JP)

( * ) Notice: Subject to any disclaimer, the term of this patent is extended or adjusted under 35 U.S.C. 154(b) by 0 days.

(21) Appl. No.: 11/044,337

(22) Filed: Jan. 28, 2005

(65) Prior Publication Data
US 2005/0185764 A1   Aug. 25, 2005

(30) Foreign Application Priority Data
Jan. 28, 2004   (JP) .............................. 2004-019419

(51) Int. Cl.
*H01J 35/24* (2006.01)
(52) U.S. Cl. .................... 378/135; 378/136; 378/134
(58) Field of Classification Search ........ 378/134–136; H01J 35/24
See application file for complete search history.

(56) References Cited

U.S. PATENT DOCUMENTS

| | | | | |
|---|---|---|---|---|
| 2,290,226 A | * | 7/1942 | De Mond | 378/134 |
| 3,949,229 A | * | 4/1976 | Albert | 378/98.6 |
| 4,360,735 A | * | 11/1982 | Seifert | 378/134 |
| 5,267,296 A | * | 11/1993 | Albert | 378/113 |
| 6,269,144 B1 | * | 7/2001 | Dube et al. | 378/71 |

FOREIGN PATENT DOCUMENTS

JP   B2-2848944   11/1998

* cited by examiner

*Primary Examiner*—Craig E. Church
*Assistant Examiner*—Krystyna Suchecki
(74) *Attorney, Agent, or Firm*—Oliff & Berridge, PLC

(57) ABSTRACT

To solve a difference in an emitting directions by switching the types of X-rays. An X-ray generator comprises: an anticathode unit 3 in which a plurality of anticathode parts 2 (2A and 2B) that emit X-rays by collision of thermoelectrons are disposed side by side; a cathode 4 for releasing the thermoelectrons toward the anticathode parts 2A and 2B on the anticathode unit 3; and a cathode moving mechanism that switches the anticathode parts, against which the thermoelectrons from the cathode 4 collide by moving the cathode 4 along the diction of aligning anticathode parts 2A and 2B. In such an X-ray generator, an optical element 6 is arranged, which emits incident X-rays R1 and R2, in a taking-out route of the X-rays emitted from the anticathode parts 2, as diffracted X-rays R11 and R12, and also an adjustment mechanism 7 that aligns emitting directions of the diffracted X-rays with respect to the incident X-rays emitted from each anticathode part, to one direction, when the anticathode parts, against which the thermoelectrons from the cathode collide, are switched by moving the cathode.

5 Claims, 3 Drawing Sheets

X-RAY GENERATOR AND ADJUSTING METHOD OF THE SAME

BACKGROUND OF THE INVENTION

1. Field of the Invention

The present invention relates to an X-ray generator and a method for adjusting the same.

2. Description of the Related Art

As an X-ray source at a laboratory level in single crystal structure analysis using X-rays, mainly Cu—Kα rays and Mo—Kα rays are used. The former is mainly used for the analysis of an organic compound and the latter is mainly used for the analysis of an inorganic compound Accordingly, in the case of, for instance, an X-ray diffractometer shared in the analysis of the organic compound and the analysis of the inorganic compound, an X-ray source of the X-ray generator needs to be changed, in accordance with samples of a user.

In the case of an X-ray generator which radiates X-rays from a surface of an anticathode (target) by colliding thermoelectrons emitted from a cathode (filament) against the anticathode, the material of the anticathode to be collided with thermoelectrons needs to be changed for changing the types of X-ray outputted.

As a method of changing the material of the anticathode against which the thermoelectrons collide, conventionally, it is a common practice to detachably form the anticathode on the X-ray generator in advance, and by changing the anticathode, multiple kinds of X-rays can be outputted with one X-ray generator.

However, it is generally not easy to make the anticathode of the X-ray generator an easily detachable structure. Especially, in the case of a rotary anticathode type X-ray generator to obtain large volume or high intensity X-rays, there are fundamental difficulties in making the anticathode itself an easily detachable structure, because a coolant must be circulated in the anticathode to cool the anticathode, the anticathode itself serves as a movable portion rotating at a high speed, the circumferences of the cathode and the anticathode are required to be a vacuum atmosphere, and so on. Even when such difficulties are overcome, there are still problems that changing work of the anticathode is complicated, and a manufacturing cost is significantly increased.

For this reason, the X-ray generator has been developed, in which a plurality of anticathodes are previously prepared, and the anticathodes against which thermoelectrons collide, are switched by moving the cathode that emits the thermoelectrons (see, for instance, Patent Document 1). This X-ray generator is provided with plural kinds of anticathodes on an anticathode unit and the cathode corresponding to the anticathode unit is installed so that it is movable along an arranging direction of the anticathode parts on the anticathode unit by an cathode moving mechanism. Then, by switching the anticathode parts, against which the thermoelectrons collide, by moving the position of the cathode, the types of X-rays outputted can be changed.

(Document 1) Japanese Patent Bulletin No. 2848944

For instance, when an optical element having a layer structure is arranged in a taking out route of the X-rays of an X-ray generator in order to make the X-rays irradiating a sample monochromatic, if the types of X-rays to be outputted is changed by moving the position of the cathode as described above, the direction of the X-rays coming from the optical element also changes. Therefore, the problem is that the above-described situation must be corrected on the side of the optical system such as a goniometer, and much time is spent for adjusting the optical system.

SUMMARY OF THE INVENTION

The present invention is provided in view of the above-described circumstances, and an object of the present invention is to provide an X-ray generator capable of easily solving differences in an emitting direction caused by switching of X-ray types, and capable of reducing adjustment as much as possible on the side of an optical system, and a method of adjusting the same.

A first aspect of the present invention provides an X-ray generator, comprising:

an anticathode unit in which a plurality of anticathode parts radiating X-rays by collision of thermoelectrons are disposed side by side;

a cathode to release the thermoelectrons towards one of the anticathode parts on the anticathode unit; and a cathode moving mechanism to switch the anticathode parts against which the thermoelectrons from the cathode collide, by moving the cathode along a direction of the aligning anticathode parts on the anticathode unit, wherein an optical element that emits incident X-rays as diffracted X-rays is arranged in a taking-out route of the X-rays radiated from the anticathode parts, and by adjusting an angle of the optical element, an adjustment mechanism is also provided to align emitting directions of the diffracted X-rays with respect to the incident X-rays emitted from each anticathode, to one direction, when the anticathode parts, against which the thermoelectrons from the cathode collide, are switched by moving the cathode.

A second aspect of the present invention provides the X-ray generator according to the first aspect of the present invention, wherein the anticathode unit is formed in rotary anticathode type including a unit main body having a drum-like shape and a plurality of cathode parts provided on the outer peripheral surface of the unit main body in a belt-like shape. In the adjustment mechanism, the angle is adjusted by slightly turning the optical element around a shaft, the shaft being vertical to a diffraction plane including a rotary shaft of the anticathode unit of the rotary anticathode type, and passing through almost the center of the surface of the optical element.

A third aspect of the present invention provides an adjusting method of the X-ray generator according to the first aspect or the second aspect of the present invention, wherein the angle of the optical element to be adjusted by the adjustment mechanism is controlled in association with the position of the cathode that moves by the cathode moving mechanism, so as to obtain an incident angle satisfying Bragg's condition expressed by:

$$2d \cdot \sin\theta = n\lambda$$

(where, θ: incident angle of the X-ray made incident to an optical element d: intervals between lattice planes of optical element λ: wavelength of X-ray n: positive integer).

Thus, when the anticathode parts, against which the thermoelectrons from the cathode collide, are switched, the emitting directions of the diffracted X-rays with respect to the incident X-rays emitted from each cathode part are aligned to one direction.

A fourth aspect of the present invention provides a method for adjusting the X-ray generator according to the third aspect of the present invention, wherein Cu (copper) and Mo (molybdenum) are provided as the cathode parts, and the emitting direction of n-th diffracted X-ray with respect to Cu—Kα ray made incident to the optical element is made identical to the emitting direction of the 2n-th diffracted X-ray with respect to Mo—Kα ray.

According to the present invention, the optical element emitting the incident X-rays as the diffracted X-rays is arranged in the taking-out route of the X-ray emitted from the anticathode parts, and the angle of the optical element is made adjustable by the adjustment mechanism. Therefore, the emitting directions of the diffracted X-rays with respect to the incident X-rays emitted from each anticathode can be aligned to one direction, when the anticathode parts, against which the thermoelectrons from the cathode collide, are switched by moving the cathode. Accordingly, even when the types of the X-ray are switched, labor for adjusting the optical system on the side of the diffractometer can be minimize.

Specifically, for example, by providing Cu (copper) and Mo (molybdenum) as the anticathode parts, the device is made to be capable of using the Cu—Kα ray and the Mo—Kα ray by switching. In this case, twice the wavelength 0.71 Å of the Mo—Kα ray (1.42 Å) is closely related to the wavelength 1.54 Å of the Cu—Kα ray. Therefore, the angle of the optical element and the moving position of the cathode are determined so as to make the emitting direction of the n-th diffracted X-ray with respect to the Cu—Kα ray made incident to the optical element, and the emitting direction of the 2n-th diffracted X-ray with respect to the Mo—Kα ray, identical to each other. Then, the posture of the optical element is adjusted to the angle thus determined, and the position of the cathode is also adjusted. Thus, the emitting directions of the X-rays from the optical element can be aligned to one direction by simple adjustment.

BRIEF DESCRIPTION OF THE DRAWINGS

FIG. 2A is a view showing the manner of diffraction before aligning emitting direction of the diffracted X-rays, and FIG. 2B is a view showing the manner of diffraction after aligning the emitting directions of the diffracted X-rays.

DETAILED DESCRIPTION OF THE PREFERRED EMBODIMENT(S)

Figure 1:
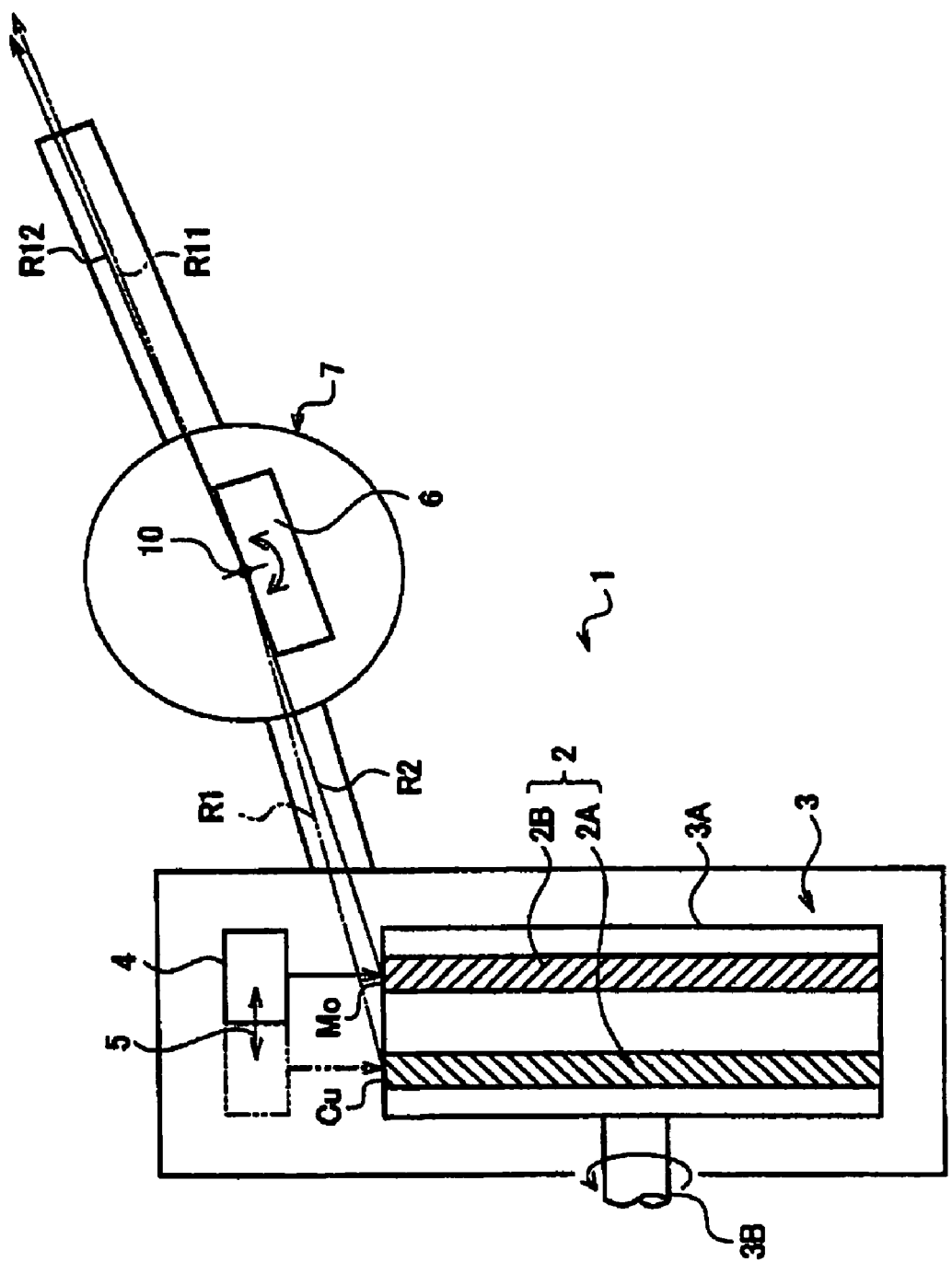
FIG. 1 is a schematic diagram of an X-ray generator 11 of an embodiment of the present invention.

Preferred embodiment of the present invention will be explained below referring to the drawings.

FIG. 1 is a schematic diagram of an X-ray generator 1 in the embodiment. The X-ray generator 1 comprises:

an anticathode unit 3 in which a plurality of anticathode parts 2 (2A and 2B) to emit X-rays by being collided with thermoelectrons are disposed side by side;

a cathode 4 to release the thermoelectrons towards one of the anticathode parts 2 on the anticathode unit 3;

a cathode moving mechanism 5 (shown by an arrow) to switch the anticathode parts 2, against which thermoelectrons from the cathode 4 collide, by moving the cathode 4 in an aligning direction of the anticathode parts 2 on the anticathode unit 3;

an optical element 6 disposed in a taking-out route of the X-rays emitted from the anticathode parts 2, to emit incident X-rays as diffracted X-rays.

The anticathode unit 3 is formed in a rotary anticathode type, provided with a plurality of anticathode parts 2 in a belt-like shape around the outer peripheral surface of a unit main body 3A having a drum-like shape. Thus, by turning a rotary shaft 3B, the unit main body 3A is rotated. As the anticathode parts 2 of the anticathode unit 3, a copper surface Cu (symbol 2A) and a molybdenum surface Mo (symbol 2B) are provided.

The optical element 6 is provided to avoid superimposing of unnecessary noise on the X-rays coming into an optical system such as a goniometer or the like, and has a layered structure having periodicity of d to make the X-rays to irradiate a sample monochromatic. An adjustment mechanism 7 to adjust the emitting directions of the diffracted X-rays by adjusting the angle of the optical element 6 is annexed to the optical element 6. In the adjustment mechanism 7, the optical element 6 is slightly turned around a shaft 10 to adjust an angle, the shaft 10 being vertical to a diffraction plane including a rotary shaft 3B of the anticathode unit 3 of the rotary anticathode type, and passing through almost the center of the surface of the optical element 6.

The adjusting mechanism 7 functions to align the emitting directions of the X-rays R11 and R12 diffracted by the optical element 6 with respect to the incident X-rays R1 and R2 emitted from each of the anticathode parts 2 (2A and 2B), to one direction, when the anticathode parts 2, against which the thermoelectrons from the cathode 4 collide, are switched by moving the cathode 4.

The condition for emitting the diffracted X-rays R11 and R12 by the optical element 6 is established when the Bragg's condition is satisfied as follows:

$$2d \cdot \sin \theta = n\lambda$$

(where, θ: incident angle of the X-ray made incident to an optical element d: intervals between lattice planes of optical element λ: wavelength of X-ray n: positive integer)

Since d and λ are predetermined values, when an incident angle to the optical element 6 satisfies predetermined conditions, the diffracted X-rays are emitted. Since when copper Cu (2A) is selected as the cathode part 2, the wavelength of radiated Cu—Kα rays is 1.54 Å, and when molybdenum Mo (2B) is selected as the anticathode part 2, the wavelength of radiated Mo—Kα rays is 0.71 Å. It is found that according to the aforementioned Bragg's condition, twice the wavelength of the Mo—Kα rays 0.71 Å to the wavelength of the Cu—Kα rays 1.54 Å provides angles θ of diffraction close to each other. Therefore, when the n-th condition is satisfied for the Cu—Kα rays, the 2n-th condition may be satisfied for the Mo—Kα rays.

Figure 2A:
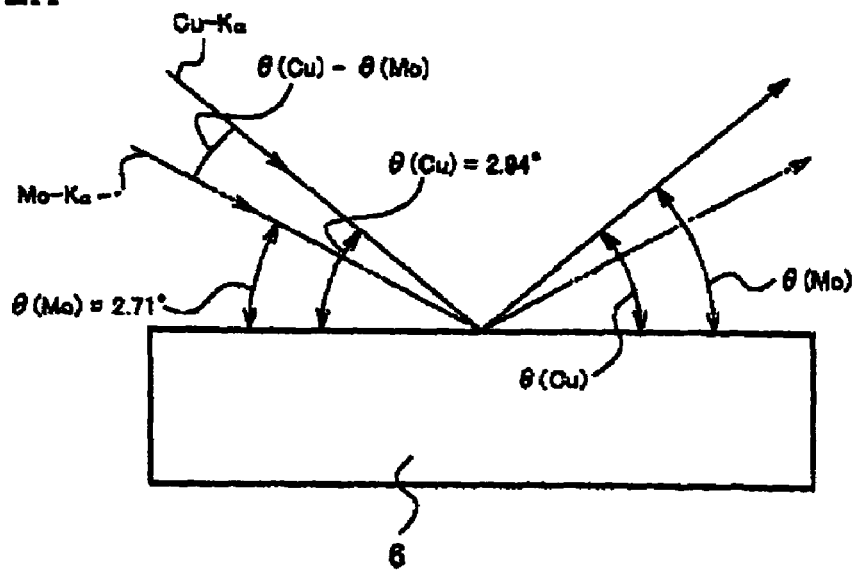
FIGS. 2A and 2B are views explaining a principle of the X-ray generator.
Figure 2B:
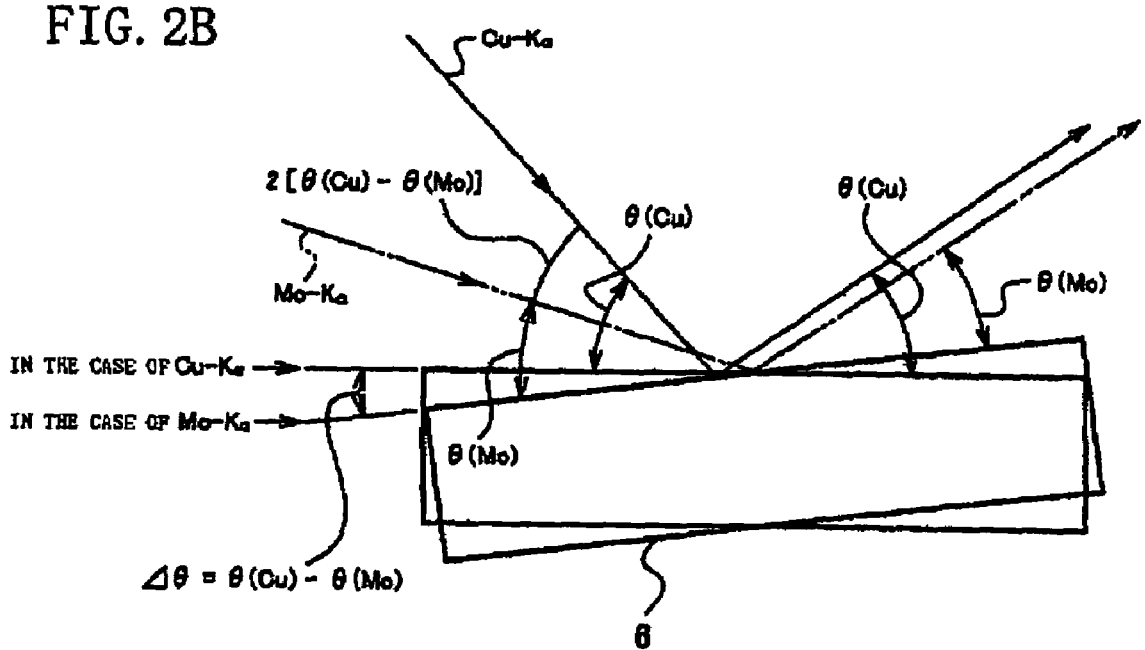

For instance, when an interval d of the crystal lattice planes of the optical element 6 is 15 Å, as shown in FIG. 2A, a diffraction in n=1 appears at θ (Cu)=2.94° for the wavelength of 1.54 Å of the Cu—Kα rays whereas a diffraction in n=2 appears at θ (Mo)=2.71° for the wavelength of 0.71Å of the Mo—Kα rays. In order to align the emitting directions to one direction, using this close relation with each other, as shown in FIG. 2B, the optical element 6 may be turned by Δθ=θ(Cu)−θ(Mo). At this time, difference in incident directions of Cu—Kα rays and Mo—Kα rays widens by the angle of 2[θ(Cu)−θ(Mo)].

Figure 3:
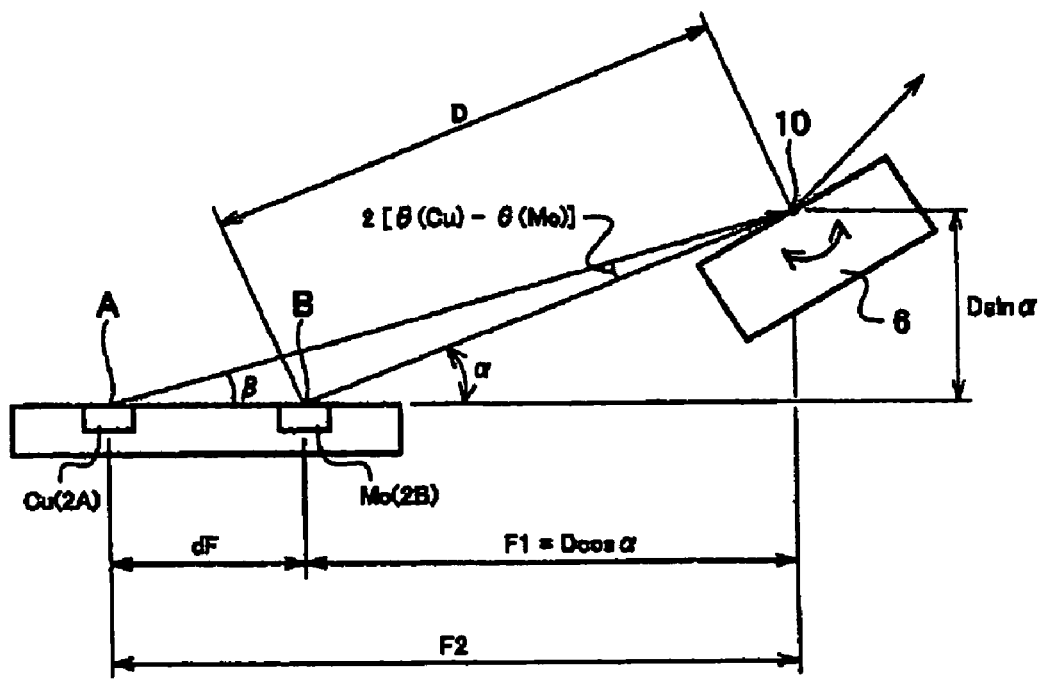
FIG. 3 is a view for explaining a principle of adjustment in the X-ray generator.

Thus, when the optical element 6 is turned by the adjusting mechanism 7 by an angle of Δθ, it is necessary to control the position of the cathode 4, which moves by the cathode moving mechanism, in relation to the change in the angle θ of the optical element 6, so as to obtain the incident angle θ sating the Bragg's condition. Specifically, as shown in FIG. 3, a distance dF (control amount when moving the anticathode) between a focal center B on the molybdenum (Mo) plane and a focal center A on the cupper (Cu) plane on the rotary anticathode surface can be calculated as below.

When a distance between a perpendicular drawn onto an extension line on the surface of the rotary anticathode from the center 10 of the optical element 6 and the focal center A on the copper (Cu) plane is set to be F2, and a distance between the above-described perpendicular and the focal center B on the molybdenum (Mo) plane is set to be F1, the equation is expressed by $$dF = F2 - F1$$

When the n-th angle of diffraction to the Cu—Kα ray is set to be θ (Cu), the 2n-th angle of diffraction to the Mo—Kα ray is set to be θ (Mo), a take-out angle of the X-ray beam based on molybdenum is set to be α, and the distance between the focal center B based on molybdenum and a surface center (axis 10) of the optical element 6 is set to be D, the equations are expressed by:

$$F1 = D \cdot \cos \alpha$$

$$F2 = D \cdot \sin \alpha / \tan(\alpha \pm 2[\theta(Cu) - \theta(Mo)])$$

where, the symbol ± depends on a direction of the optical element 6.

The direction in FIG. 3 corresponds to minus.

Accordingly, if positional relations (D, α) between the anticathode parts 2 (2A and 2B) and the optical element 6 is determined, when the angle of the optical element 6 is adjusted by Δθ=θ(Cu)−θ(Mo), the emitting directions of the diffracted X-rays from the optical element 6 can be aligned to one direction even in the case of Cu—Kα rays as well as in the case of Mo—Kα rays, in short, even when the ray source is switched to any rays, by moving the position of the cathode 4 by the dimension of dF. As a result, adjusting of the optical system on the side of the diffractometer can be minimized at the time of switching the ray sources of the X-rays to simplify the adjustment work.

Since the X-ray generator 1 and adjusting method according to the present embodiment have the above-described structure and functions, change of ray sources can be easily and rapidly performed in the following fields and high usability can be exhibited.

For instance, in a two-dimensional detector (an imaging plate and a CCD or the like) which has been widely used in recent years, since its sensitive area is limited, in order to collect a diffraction image effectively, as clearly shown by the Bragg's condition, Mo—Kα rays, by which a diffracted image is rather reduced and observed, is selected if spatial resolution on a detector allows. On the other hand, determination of an absolute structure using an abnormal dispersibility of X-rays is an important method, which can be never achieved by other structural analyzer such as an MNR or the like. In this method, there is no problem whichever ray source of Mo or Cu is selected, when an atom having a relatively large atomic number (for instance, sulfur (S) or atoms having larger in atomic number than sulfur) is contained in a molecule for analysis. However, in a case of an organic compound composed of only carbon (C), nitrogen (N), oxygen (O), and hydrogen (H) is for instance, Mo—Kα rays are not put to practical use because the abnormal dispersibility is significantly insufficient. Accordingly, in this case, the Mo—Kα rays are required to be changed to the Cu—Kα rays. However, an ordinary structural analysis is carried out using Mo—Kα rays, and only necessary data to determine an absolute structure may be measured with Cu—Kα rays. The X-ray generator of this embodiment can easily and rapidly change the ray source even in such a case.

What is claimed is:

1. An X-ray generator, comprising:
    an anticathode in which a plurality of anticathode parts radiating X-rays by collision of thermoelectrons are disposed side by side;
    a cathode to release the thermoelectrons towards one of the anticathode parts on said anticathode unit; and
    a cathode moving mechanism to switch the anticathode parts, against which the thermoelectrons collide from a cathode, by moving the cathode in an aligning direction of the anticathode parts on the anticathode unit,
    wherein an optical element that emits incident X-rays as diffracted X-rays is arranged in a taking-out route of the X-rays radiated from the anticathode parts, and by adjusting an angle of the optical element, an adjustment mechanism is also provided to align emitting directions of the diffracted X-rays with respect to the incident X-rays emitted from each anticathode, to one direction, when the anticathode parts, against which the thermoelectrons from the cathode collide, are switched by moving the cathode.

2. The X-ray generator according to claim 1,
    wherein said anticathode unit is formed in a rotary anticathode type including a unit main body having a drum shape, and a plurality of anticathode parts provided on a peripheral surface of the unit main body in a belt-like shape,
    wherein the angle is adjusted by slightly turning the optical element around a shaft, the shaft being vertical to a diffraction plane including a rotary shaft of the anticathode unit of the rotary anticathode type, and passing through almost the center of the surface of the optical element.

3. An adjusting method of the X-ray generator according to claim 1,
    wherein an angle of the optical element to be adjusted by the adjustment mechanism is controlled in association with the position of the cathode that moves by the cathode moving mechanism, so as to obtain an incident angle satisfying Bragg's condition expressed by:

$$2d \cdot \sin \theta = n\lambda$$

(where, θ: incident angle of the X-ray made incident to an optical element
    d: intervals between lattice planes of optical element
    λ: wavelength of X-ray
    n: positive integer),
    and when the anticathode parts, against which the thermoelectrons from the cathode collide, are switched, the emitting directions of the diffracted X-rays with respect to the incident X-rays emitted from each cathode part are aligned to one direction.

4. The adjusting method of the X-ray generator according to claim 3,
    wherein Cu (copper) and Mo (molybdenum) are provided as said cathode parts and the emitting directions of n-th diffracted X-rays with respect to Cu—Kα rays made incident to the optical element are made identical to the emitting directions of the 2n-th diffracted X-rays with respect to Mo—Kα rays.

5. An adjusting method of the X-ray generator according to claim 2,
wherein an angle of the optical element to be adjusted by the adjustment mechanism is controlled in association with the position of the cathode that moves by the cathode moving mechanism, so as to obtain an incident angle satisfying Bragg's condition expressed by:

$$2d \cdot \sin \theta = n\lambda$$

(where, $\theta$: incident angle of the X-ray made incident to an optical element d: intervals between lattice planes of optical element $\lambda$: wavelength of X-ray n: positive integer), and when the anticathode parts, against which the thermoelectrons from the cathode collide, are switched, the emitting directions of the diffracted X-rays with respect to the incident X-rays emitted from each cathode part are aligned to one direction.

* * * * *